United States Patent [19]
Williams

[11] Patent Number: 5,587,795
[45] Date of Patent: Dec. 24, 1996

[54] SELF ALIGNING SUBSTRATE TRANSMITTANCE METER

[76] Inventor: Robert D. Williams, 5374 S. Datura St., Littleton, Colo. 80120

[21] Appl. No.: 502,255

[22] Filed: Jul. 13, 1995

[51] Int. Cl.⁶ .................................................. G01N 21/00
[52] U.S. Cl. .......................... 356/432; 356/244; 359/903
[58] Field of Search ................................ 356/432, 244; 359/903

*Primary Examiner*—Frank Gonzalez
*Assistant Examiner*—Jason D. Eisenberg
*Attorney, Agent, or Firm*—Floyd E. Anderson

[57] ABSTRACT

A portable substrate transmittance meter includes a remote transmitter and a remoter receiver for measuring a light transmittance of a substrate that does not have an edge available for sliding a base meter thereover, for example a fixed window on a vehicle. The remote transmitter is releasably attached to one side of the window with a donut shaped magnet resting thereagainst. The remote transmitter includes a light transmitter for emitting a predetermined light signal through a center of the donut shaped magnets and on through the fixed window. The remote receiver is place on the other side of the fixed window opposite the remote transmitter. Donut shaped magnets of the remote receiver cause the remote receiver to attract towards the remote transmitter in proper alignment therewith. A light receiver of the remote receiver receives the transmitted light for effecting a transmittance measurement of the fixed window.

19 Claims, 10 Drawing Sheets

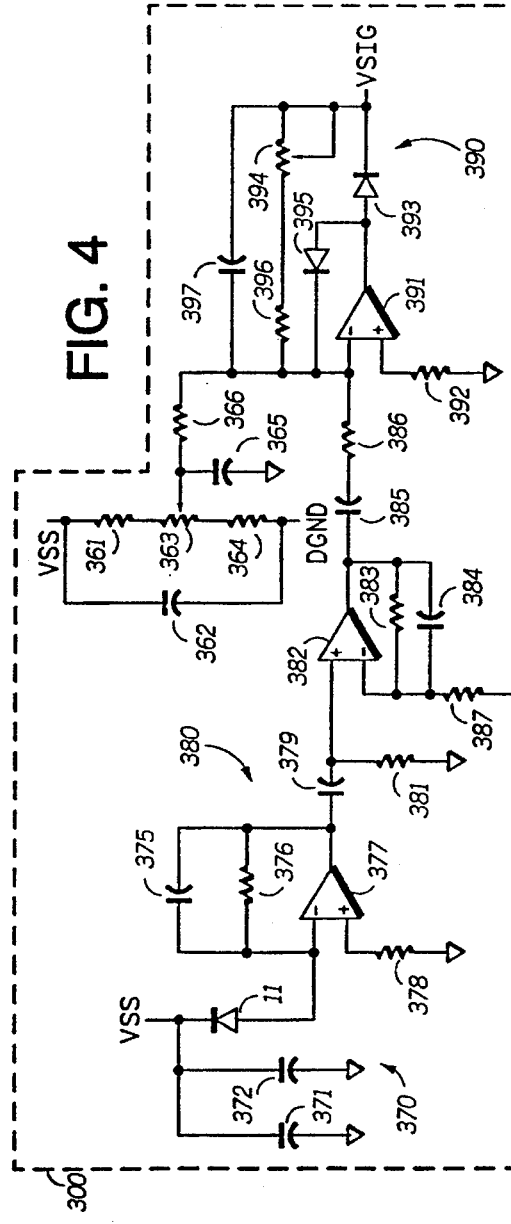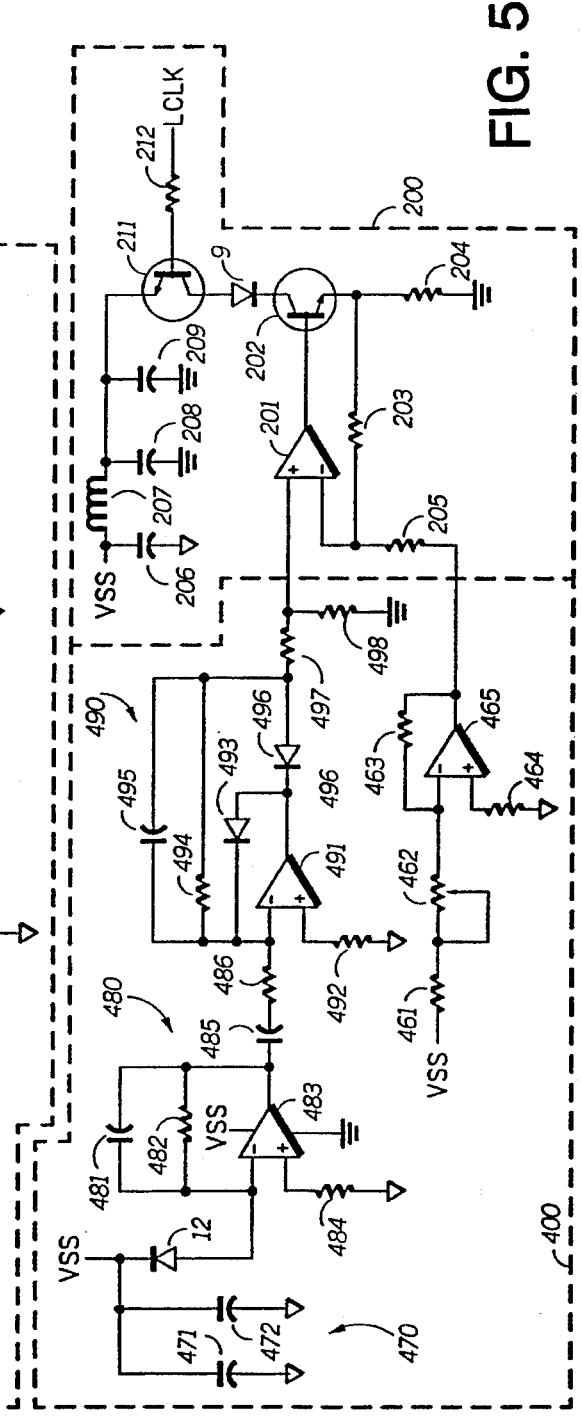

SELF ALIGNING SUBSTRATE TRANSMITTANCE METER

FIELD OF THE INVENTION

This invention relates in general to the field of light transmission measuring devices, and more particularly, to a meter for measuring the transmittance of a substrate.

RELATED APPLICATIONS

This patent application is related to pending patent application Ser. No. 08/185,039, filed Jan. 24, 1994 and assigned to the same assignee as the present application.

BACKGROUND OF THE INVENTION

There have been available over the years many apparatuses for measuring opacity or transmissivity of materials. Such apparatuses have proven useful in production areas where it is necessary to monitor not only the presence or absence of objects, but further to more accurately measure aspects of a material relating to its opacity or transmissivity. For example, an apparatus that measures opacity of a material can be used for determining the thickness of such material, which information can be used for quality control.

Still further, an opacity measurement apparatus is provided for determining a density of an effluent flowing in a furnace stack as described in U.S. Pat. No. 4,076,425, issued to Saltz. This apparatus uses a first light path directed through the effluent and a second light path external to the effluent. A ratio is determined from measurements taken from the first and second light paths for indicating the opacity of the effluent. Such apparatuses as described by Saltz, however, include several reflection mirrors and lenses and can be relatively cumbersome, complex, and sensitive.

Suzuki et al., in U.S. Pat. No. 5,231,576, teaches an apparatus for testing specimen concentrations (blood) by reflecting a light off of the specimen, which apparatus requires a 60 second delay after the switch 36 is enabled by loading a test piece. Brunnschweiler, in published patent application GB 21772102A, teaches a light transmission measuring system using a second detector 14a for controlling the intensity of the light source.

Automobile window tinting presents a field where it has become necessary to determine the transmittance property of the tinted glass. Such transmittance measurements are made ever more urgent because several states have passed legislation regulating the allowable transmittance of automobile windows. In some localities, enforcement agencies must resort to subjective tests in determining whether a given window is tinted too dark. For example, one known method of checking a window tint is accomplished by viewing a specially marked card through the window while making a visual check of visible patterns printed on the card. Enforcing such recently enacted legislation, however, requires a more scientific, accurate and repeatable measurement. For practicality purposes, this requires a portable, battery operated, transmittance meter having accurate measurement capabilities. Such a meter must not only be rugged, but also able to maintain accuracy so that any measurements taken will meet minimum evidentiary requirements in court.

One such attempt of providing a portable window transmittance meter, for use by law-enforcement personnel, for example, is described in U.S. Pat. No. 5,073,707 issued to Marcin. The apparatus described therein includes a housing having a slot which may be slipped over a window pane. A switch detects the initial entry of the window pane into the slot which almost immediately thereafter causes a light emitting diode to transmit light that is measured and stored. Since the window pane has not yet fully entered the slot, the transmittance of air is initially measured for use as a reference. A second light measurement is made approximately three seconds later when the window pane is assumed to be fully inserted. A ratio is determined between the first reference measurement and the second measurement for providing an indication of the window's transmittance.

Notwithstanding Saltz and Marcin, there still exists a need to improve both the reliability and accuracy of the transmittance meter. Specifically, Saltz's apparatus is inappropriate for portable use, and Marcin's meter may be affected by stray light, and may further produce false readings due to improper use, for example, from light scattering when the window is not properly inserted or when inserted too slowly (or moved after insertion but before the second measurement). The light scattering errors can occur from light scattered off the edge of the glass. Stray light should be accounted for and substantially eliminated for highly accurate measurements. Still further, inaccuracies may occur due to environmental conditions and circuit tolerances.

These problems are further exacerbated by the need to test those windows that are not accessible for sliding a portable window transmittance meter thereover. For example, a stationary back window or a rear window may be tinted at a different darkness level than the other movable windows. None of the heretofore known portable meters provide a capability of placing a transmitter and detector on opposing sides of such a stationary window. Other problems present themselves in such a situation, for example, even if transmitters and receivers are so placed, they must be accurately aligned, a task that can be made especially difficult given limited arm lengths.

Thus, what is needed is a portable window transmittance meter having a capability to place a transmitter and receiver on opposing sides of a substrate not having an open edge available, the transmitter and receiver being capable of self alignment so as not to depend upon an accuracy of manual alignment accuracy for such tests.

SUMMARY OF THE INVENTION

Accordingly, it is an object of the present invention to provide a substrate transmittance meter capable to measure transmittances on a substrate lacking an accessible edge.

Another object of the present invention is to provide a substrate transmittance meter capable to measure transmittances on a substrate lacking an accessible edge, such measurement easily performed by one operator.

Still another object of the present invention is to provide a window transmittance meter capable of measuring transmittances of stationary automobile windows, wherein an independent transmitter and receiver of the transmittance meter are self aligning.

According to a first embodiment of the present invention, a method for measuring a percent transmittance of a mounted substrate is provided. A remote transmitter houses a light transmitter and a first magnet, such that the light transmitter transmits a light through an opening in the housing. Similarly, a remote receiver houses a light receiver and a second magnet. The method includes the steps of placing the remote transmitter against a first surface of the mounted substrate with the first magnet substantially resting against the first surface such that the light transmitter is directed towards the first surface. The remote receiver is located against an opposing surface of the mounted substrate with the second magnet substantially against the opposing surface and substantially in a light path alignment with the remote transmitter. The remote transmitter self aligns to the remote receiver according to first and second magnetic lines of flux of the first and second magnets, respectively. The light transmitter is caused to emit a light through the mounted substrate for detection by the light receiver and the percent transmittance of the mounted substrate is thereafter determined.

According to a second embodiment of the present invention a self aligning window transmittance meter measures a light transmittance of a fixed window. The self aligning window transmittance meter includes a remote transmitter having a first housing for holding a first magnet in a predetermined alignment with a light transmitter, the remote transmitter also having an input for receiving a transmit signal. A remote receiver has a second housing for holding a second magnet in a predetermined alignment with a light receiver, the remote receiver also having an output for transmitting a transmittance signal, wherein the remote transmitter is placed against a surface of the fixed window such that the remote receiver is brought proximate to an opposing surface of the fixed window and within a magnetic flux of said first magnet such that the first and second magnets are releasably held against the surface and opposing surface, respectively, so as to cause said remote transmitter and remote receiver to self align for measuring a light transmitted through the fixed window by the light transmitter and received by the light receiver for providing a light transmittance measurement of the fixed window.

BRIEF DESCRIPTION OF THE DRAWING

FIG. 4 is a schematic diagram of a detector circuit.

FIG. 5 is a schematic diagram of a light transmitter and control circuit.

DESCRIPTION OF A PREFERRED EMBODIMENT

Figure 1B:
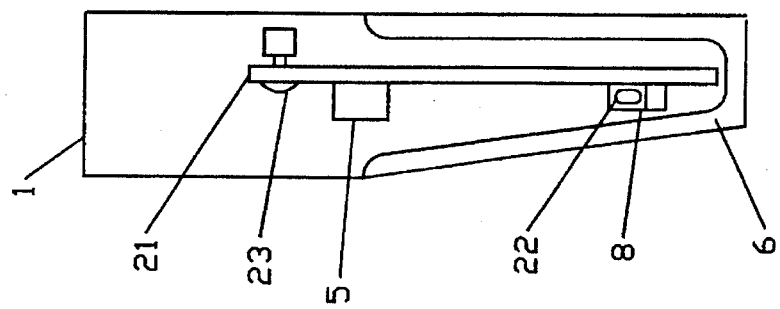
FIG. 1B is a pictorial diagram side view of the substrate transmittance meter of FIG. 1A.
Figure 1A:
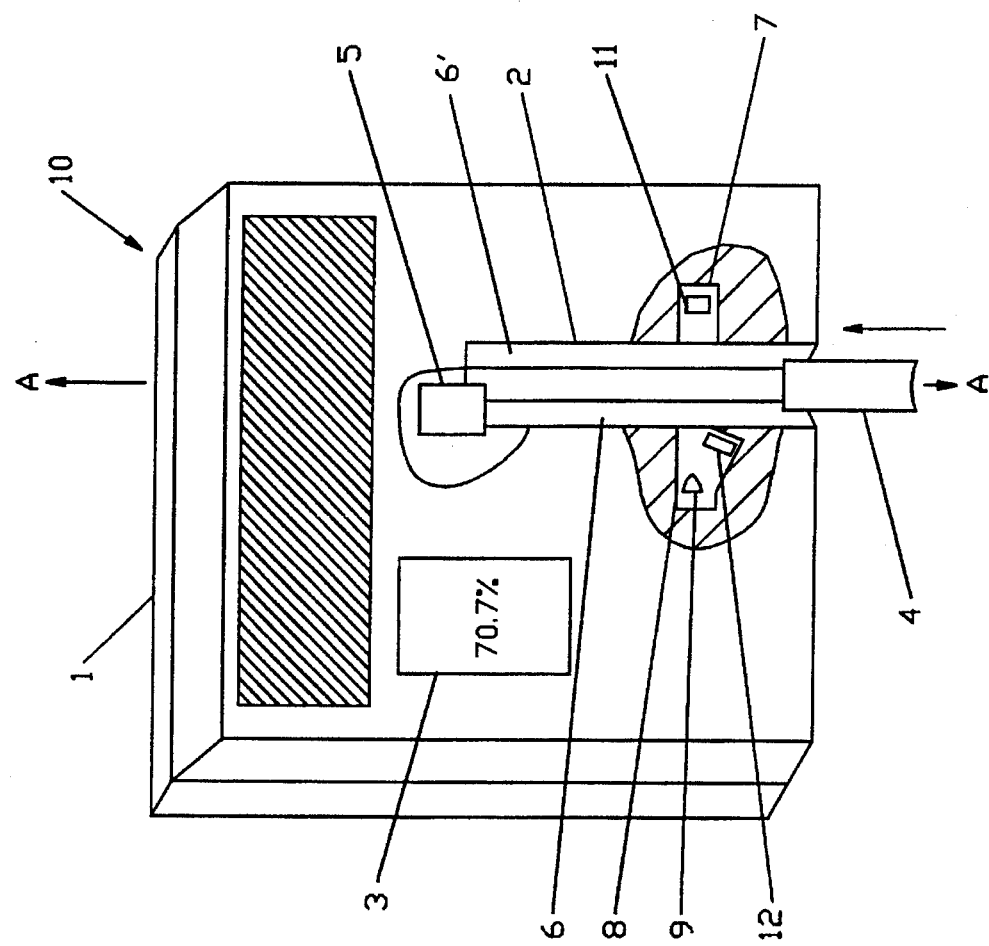
FIG. 1A is a pictorial diagram of the substrate transmittance meter.

FIG. 1A shows a pictorial diagram of a window transmittance meter, wherein the window transmittance meter (also interchangeably referred to as a base unit). The present invention comprises a meter 10 for measuring the transmittance of a substrate. The meter 10 is supported and protected by a housing 1 which includes a slot or receptacle 2 formed therein having a closed end (distal) and an open end (proximate) for sliding the housing 1 over an edge of a substrate to be measured, for example, a window pane 4. The meter 10 is normally disabled (for example, a battery is electrically disconnected therefrom). Inserting the window pane 4 completely into, or nearly completely into the slot 2, causes the window pane 4 to make physical contact with a switch or enable circuit 5 which further causes the battery (not shown) to be electrically connected to the meter 10. The switch 5, which is located at or near the closed or distal end of slot 2, can be one of many types of switches currently available. For example, the switch 5 could be accomplished by using a normally open switch which is caused to be closed by the window pane 4. Similarly, the switch 5 may be realized by use of a momentary switch that closes only momentarily when contacted. Alternately, the switch 5 need not be a mechanical switch, but rather the switch 5 could be a laser or light operated switch, etc.

While the switch 5 has been described advantageously as existing at the distal end for ensuring that the window pane 4 is properly inserted before making a measurement, one skilled in the art will appreciate that another choice of the switch 5 is a hand operated switch that powers the window transmittance meter for taking a measurement without further operator interaction. In such a case, the operator will note the change in the reading from that of air to that of the tinted window. This is accomplished by repeating the measurement every few seconds.

After the switch 5 is contacted by the window pane 4 and battery power is applied to the meter 10, a light transmitter (including, for example, a Light Emitting Diode (LED) 9 encased in a baffle 8) begins to transmit light. The transmitted light travels in two distinct light paths: first, a portion of the transmitted light shines directly onto a first light detector, for example, a photodiode 12, through a tunnel or light pipe of the baffle 8; and second, through the inserted window pane 4 and onto a second light detector (including, for example, a photodiode 11 encased in a baffle 7). The photodiode 12, also encased in the baffle 8, but angled away from the LED 9, and out of the line of sight of the photodiode 11, is used for collecting a portion of the transmitted light for control purposes. The baffles 7 and 8 (having a portion cutaway for descriptive purposes) are provided for blocking stray, and hence undesirable light, while also providing a rigid housing for protecting and properly aligning the LED 9 and the photodiodes 11 and 12. The baffle 8 has two tunnels provided therein (not shown), a first tunnel for directing light through a substrate baffle 6, and a second tunnel for allowing light to fall upon the photodiode 12. The baffle 7 has a single tunnel for collecting light through a substrate baffle 6' and onto the photodiode 11.

The baffles 7 and 8 may be constructed from many suitable materials, including, for example, urethane or ABS.

The baffle 8 is preferably constructed of an opaque plastic, urethane or neoprene type material while the baffle 7 is constructed of a dark plastic, urethane or neoprene type material. The substrate baffles 6 and 6' are each affixed around an opposing surface area of the slot 2 for conforming substantially to the substrate or window pane 4 for blocking stray and reflected lights from the photodiode 11. Preferably, the substrate baffles 6 and 6' should be made of a material that can allow the window pane 4 to be easily inserted into the slot 2 while conforming to the surface of the inserted window pane 4. This may be accomplished for example, by a rubber or urethane type material having a cloth like cover wherein the cloth like cover sufficiently contacts the window pane 4 such that stray light is effectively blocked from between the interface of the window pane 4 and the substrate baffles 6 and 6' (i.e., the window pane 4 is sandwiched between the baffles 6 and 6').

FIG. 1B provides a side view along line A of the meter 10 in FIG. 1A. A portion of the substrate baffle 6 as it sits in the slot 2 is shown with a front side of the baffle 8 now visible. From FIG. 1B, it can now be seen, that with the window pane 4 inserted into the slot 2, transmitted light from the LED 9 passes through a relatively large opening created by the substrate baffle 6 (and substrate baffle 6') while stray light is effectively blocked. In an alternative embodiment, the substrate baffle 6 (and 6') could be formed to provide only a very small hole, through which a snout (not shown) of the baffle 7 (a corresponding hole receives a snout of the baffle 8 on the opposing side of the slot) would be aligned. Thus, holes in the substrate baffles 6 and 6' and the aligned baffles 7 and 8 allow mainly only the desired light transmitted via the LED 9 to pass through the window pane 4.

The baffle 8 is shown with an oval opening or light pipe 22, which opening 22 allows the transmitted light to pass through the baffle 8 and eventually onto the photodiode 11. The LED 9, substantially centered in the opening 9, will still transmit its light effectively to the photodiode 11 even if the housing 1 is twisted in operation somewhat causing the baffle 8 to become slightly misaligned with the baffle 7. The internal surface of the opening 22 is smoothed for improving reflections of the light transmitted by the LED 9. An opening in the baffle 7 (not shown), on the other hand, is fitted substantially to the photodiode 11 and has an inside surface that is roughed or textured for reducing light reflections for minimizing stray light effects. The transmitted light, can also be generated by using a trio of LEDs, for example, a red, green and yellow LED, arranged in a triangle to provide a white light.

Based upon the transmitted light being directly received by the photodiode 11, and a portion of the transmitted light being received by the photodiode 12, a transmittance measurement is determined. Within a matter of seconds of inserting the window pane 4 into the slot 2, a transmittance measurement is displayed on a display 3 (FIG. 1A). The measurement may be held on the display 3 until the meter 10 is removed, or alternatively, a new measurement can be repeated every few seconds.

Figure 2:
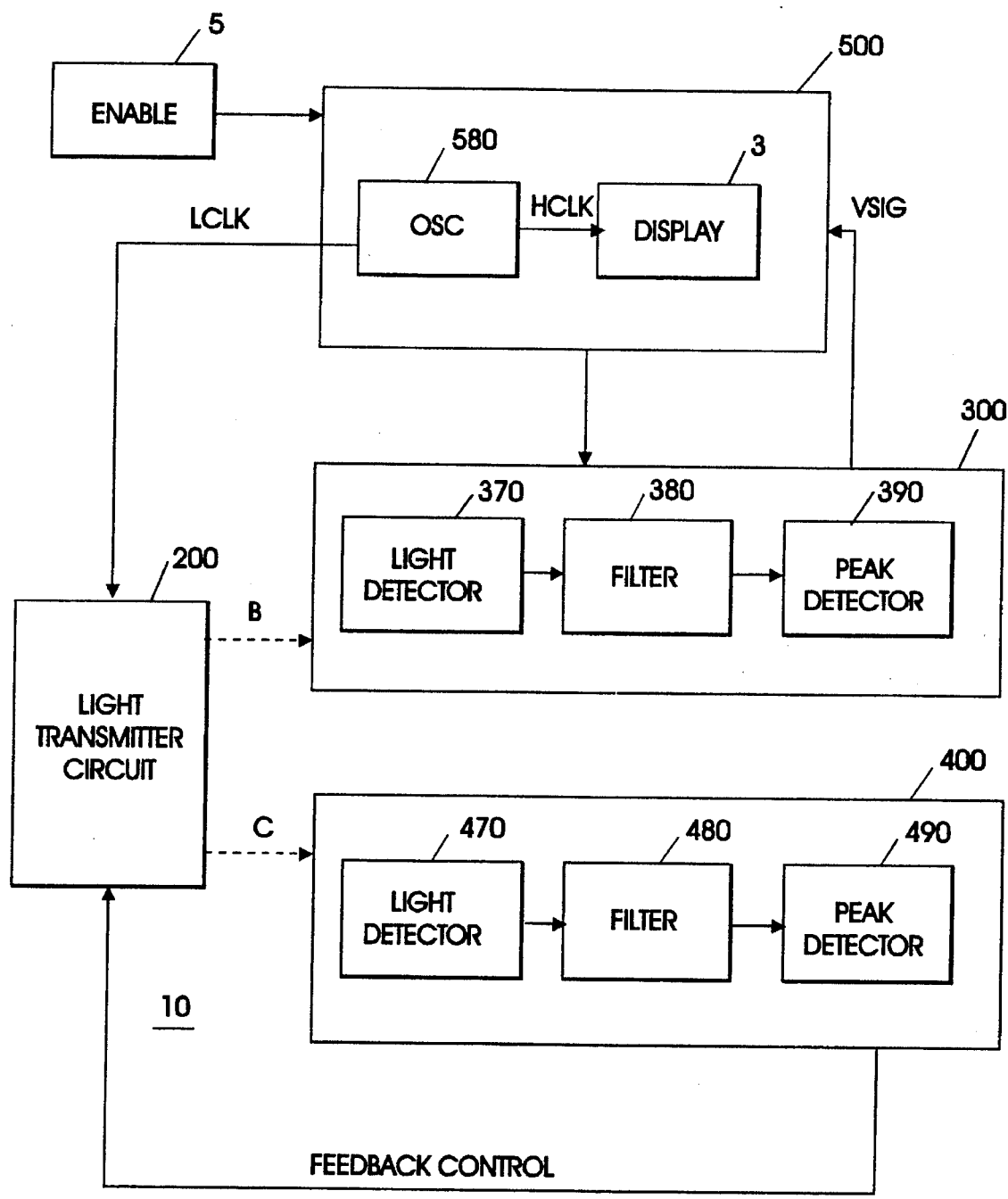
FIG. 2 is a block diagram of a circuit for enabling window transmittance measurements.

FIG. 2 shows a block diagram of the preferred embodiment of the present invention depicting the meter 10 including the enable circuit or switch 5 connected for providing power to circuitry making up the meter 10 when the window pane 4 (FIG. 1A) has been fully (or substantially) inserted into the slot 2. With power applied, a light transmitter circuit 200, which includes the LED 9, operates to provide the transmitted light to detector circuits 300 and 400, which include the photodiodes 11 and 12, respectively. The transmitted light, in the preferred embodiment, is produced from a green (approximately 560 nanometers) LED light source. As may be appreciated by one of ordinary skill in the art, a light having a differing wavelength can be used, for example, white light, without varying from the scope of the invention described herein.

A display circuit 500 includes an oscillator and display driver 580 (hereinafter display drive 580) and the display 3. A modulation signal, LCLK, generated from an oscillation signal, HCLK, of the display driver 580 is connected to the light transmitter circuit 200 wherein the modulation signal oscillates at a predetermined frequency for modulating the LED 9 and therefore the transmitted light of the light transmitter circuit 200. A frequency of three kilohertz is used in the present invention as the frequency of the modulation signal, LCLK. The oscillation frequency of the display driver 580 is set to run at approximately forty-eight kilohertz, and is connected to the display 3 for providing a needed alternating current signal thereto. The three kilohertz modulation signal is derived from the oscillation signal, HCLK.

Modulating the LED 9 (i.e., the transmitted light), in part, eliminates errors that would otherwise occur due to DC offset voltages present in the circuitry of the meter 10. Further accuracy is achieved by detecting only a band of frequencies of the transmitted light, thereby substantially immunizing the detector circuits 300 and 400 to low levels of stray light reflected off the window pane 4. The modulation signal of three kilohertz is at a substantially lower frequency than that of the oscillator signal driving the display driver 3. The modulation signal is thus divided down, for example, by sixteen, from the forty-eight kilohertz oscillator signal. As can be appreciated by those skilled in the art, the LED 9 does not absolutely require modulation, but instead, a tradeoff can be made for reducing circuit complexity at a cost of some reduction in accuracy. The tradeoff is dependent, to some degree, upon that stray light may be eliminated (creating a different complexity and cost).

The transmitted light radiates directly upon the photodiode 11 (FIG. 1A) via a light path B which forms part of a light detector circuit 370. The light detector circuit 370 generates a detect signal proportional to the level of transmitted light detected, the detect signal being connected to a filter 380 wherein the filter 380 is a band pass filter for allowing only a band of predetermined frequencies to pass therethrough. The band of frequencies, of course, encompass the frequency of the transmitted light modulated at three kilohertz. In the preferred embodiment the high frequency is set at approximately ten kilohertz and the low frequency is set at approximately one kilohertz. The relatively broad band of pass frequencies allow the modulation frequency to vary substantially without significantly degrading amplitude response. If the LED 9 is not modulated then the filter 380 could be omitted.

The filter 380 outputs a filtered detect signal to a peak detector 390 for detecting only the positive peaks of the filtered detect signal. The peak detected signal, VSIG, is then provided to the display circuit 500 for calculating and displaying the percent transmittance of the window pane 4.

The detector circuit 400 comprises a light detector which includes the photodiode 12 (FIG. 1A) located just beyond the direct line of sight of the photodiode 9. The photodiode 12 receives the transmitted light via light path C, for providing a reference detect signal to a filter 480 which filters out those frequencies below about one kilohertz. Optionally, a filtered indirect light detect signal of the filter 480 is connected to an input of a peak detector 490. The peak detector 490 detects only the negative peaks of the filtered indirect light detect signal. The peak detector 490 provides a feedback signal to the light transmitter circuit 200 (negative feedback) for controlling an operating point of the light transmitter circuit 200.

Figure 3:
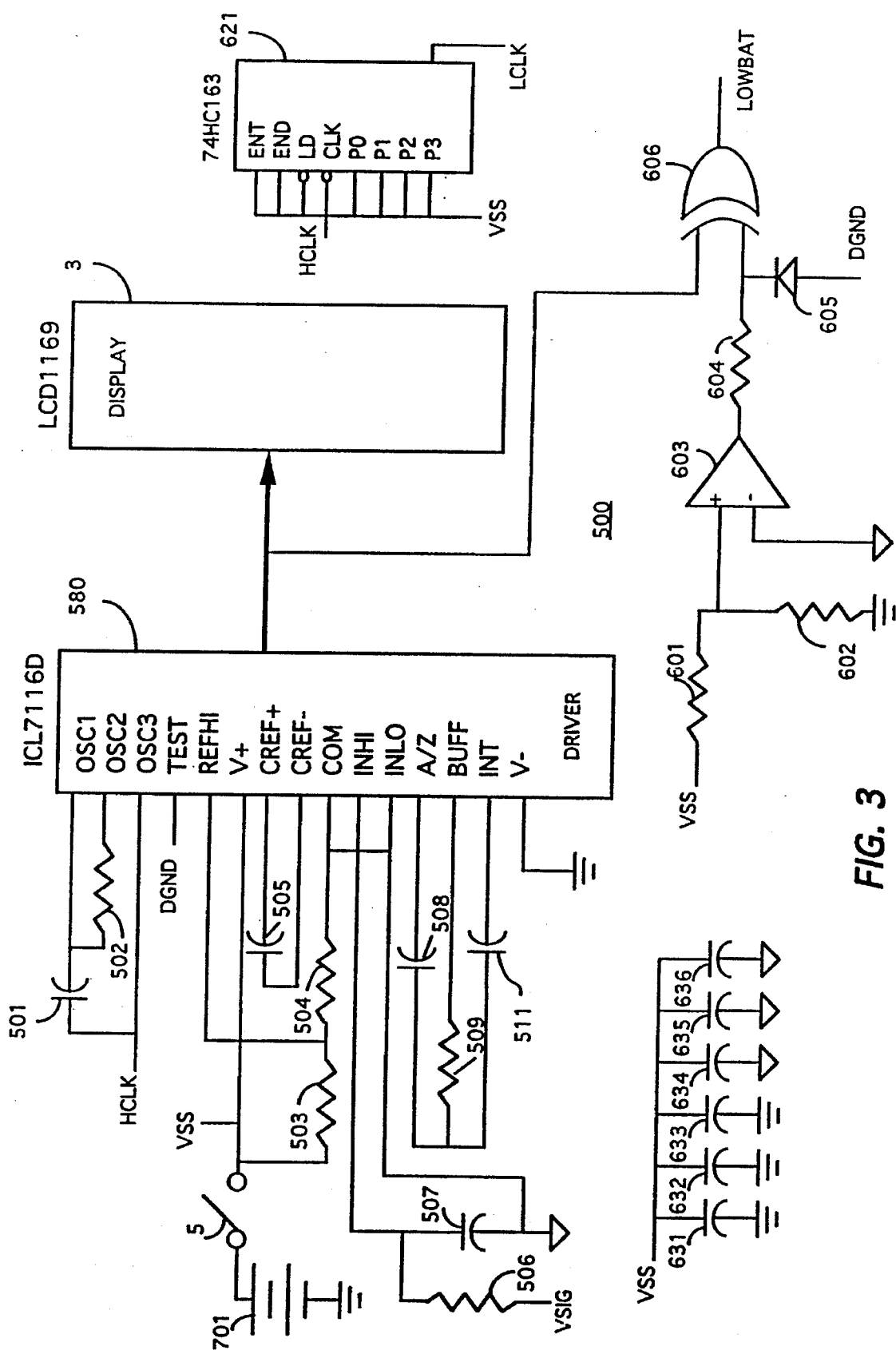
FIG. 3 is a schematic diagram of the display driver and display.

FIG. 3 shows the display circuit 500 of the meter 10 in schematic diagram form. A battery 701, for example a nine volt battery, is connected between ground and a first terminal of the switch 5. When the switch 5 is closed by the presence of the window pane 4, power is applied to the display circuit 500, and more specifically to a V+ input of the display driver 580. The display driver 580 may be realized by an integrated circuit, for example, ICL71165 or TC7106TPL. The display driver 580 provides two regulated voltages. An analog ground voltage (COM) has a magnitude substantially equal to a voltage of the battery 701 less 2.8 volts. A digital ground voltage (DGND) has a magnitude substantially equal to the voltage of the battery 701 voltage less five volts. Such regulated voltages are then provided to power other portions of the circuitry of the meter 10.

The oscillator signal, HCLK, is also supplied by the display driver 580, in this case the forty-eight kilohertz signal, as determined by a capacitor 501 and a resistor 502. A divide by sixteen circuit 621, for example, 74HC163, divides the forty-eight kilohertz oscillator signal down to the desired three kilohertz signal, LCLK, for modulating the transmitted light accordingly. Outputs of the display driver 580 are connected to the LCD display 3, for example, LCD1169. Reference levels and the input signal, VSIG, from the peak detector 390 are input into the display driver by devices 503 through 511.

A magnitude of the voltage of the battery 701 is monitored to determine whether the magnitude is sufficient to properly operate the meter 10. If the magnitude of the voltage of the battery 701 falls below a predetermined threshold, as determined by the voltage divider connected resistors 601 and 602, then a comparator 603 connected thereto outputs a signal to an exclusive-Or gate 606. An output of the exclusive-Or gate 606, LOWBAT, indicates a low voltage condition which can be displayed on the display 3.

Referring to FIG. 4, the detector circuit 300 includes the photodiode 11 having a cathode connected to VSS and to ground via parallel connected capacitors 371 and 372. An anode of the photodiode 11 is connected to an inverting input of the filter 380. The filter 380 includes series connected low pass and high pass filters realized by transimpedance amplifiers 377 and 382, respectively. The low pass filter is realized by parallel connected capacitor 375 and resistor 376 across an output and the inverting input of the amplifier 377. A resistor 378 connects a non-inverting input of the amplifier 377 to ground. RC network made of capacitor 379 and resistor 381 connects an output of amplifier 377 to a non-inverting input of the amplifier 382 (the high pass filter). Parallel connected capacitor 384 and resistor 383 are connected across an output of the amplifier 382 and an inverting input. Resistor connects the inverting input of the amplifier 382 to ground. Series connected capacitor 385 and resistor 386 connect the output of the amplifier 382 to an inverting input of an amplifier 391. The peak detector 390 is comprised of devices 391 through 397 and 361 through 366. VSIG is output from the peak detector 390 for indicating the transmittance of the window pane 4.

The high pass filter, as previously stated is set at approximately ten kilohertz while the low pass filter is set at approximately one kilohertz. The low pass and high pass filters thus form a band pass filter (380) having a substantially broad frequency pass band relative to the three kilohertz transmitted light frequency. The locations of the poles and zeros may vary to reflect the wavelength of the transmitted light. Also, by keeping the poles and zeros at least one octave from the modulation frequency, frequency variation over temperature will cause insignificant variation in amplitude response.

Referring to FIG. 5, the detector circuit 400 includes the photodiode 12 for receiving the portion of the transmitted light and having a cathode connected to ground by capacitors 471 and 472. An anode of the photodiode 12 is connected to an inverting input of transimpedance amplifier 483. Devices 481 through 486 form the low pass filter 480 in a manner similar to the low pass filter described above. An output of the lowpass filter 480 is connected to an input of the negative peak detector 490 made up of devices 491 through 498.

An output of the optional peak detector 490 is connected to a non-inverting input of amplifier 201 which acts both as a driver and a subtracter for controlling the LED 9. Series connected resistors 461 and 462, connected between ground and an inverting input of the amplifier 465 provide for manual calibration of an operating point of the LED 9, for example, approximately thirty milliamps through the LED 9. Resistors 463 and 464 are connected for setting the gain of the amplifier 465. Resistor 205 connects an output of the amplifier 465 to an inverting input of the amplifier 201. An output of the amplifier 201 drives a base of transistor 202. An emitter of the transistor 202 is connected to the inverting input of the amplifier 201 via a resistor 203 and to ground via a resistor 204. Transistor 202 can thus be biased to control a current flow through the LED 9. The LED 9 is modulated by the signal LCLK which is connected to the base of a transistor 211 by a resistor 212. A collector of the transistor 211 is connected to an anode of the LED 9 while a cathode of the LED 9 is connected to a collector of the transistor 202. A filter circuit made up of devices 206 through 209 connect the emitter of the transistor 211 to ground, COM, and VSS. Additionally, parallel connected capacitors 631 through 636 (FIG. 3) provide a filter between VSS and ground.

Figure 6:
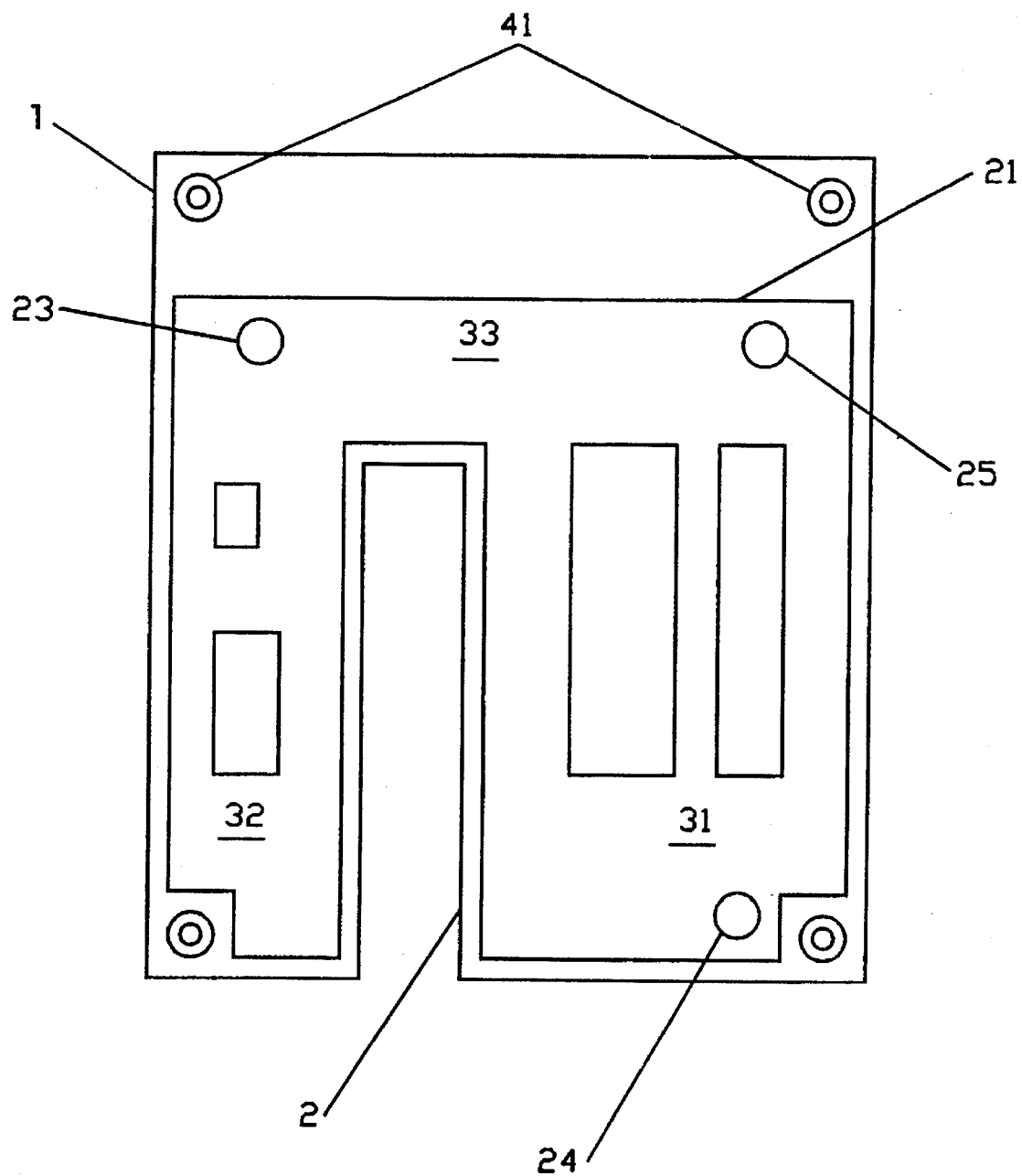
FIG. 6 is a pictorial diagram of a printed circuit board mounted within the housing of the substrate transmittance meter.

Referring now to FIG. 6, a circuit board 21, for holding circuit components of the meter 10 is shown as mounted within the housing 1 (see FIGS. 1A and 1B). The circuit board 21 includes an upper portion 33, and a wide leg 31 and a narrow leg 32 situated on opposing sides of the slot 2. Three standoffs, 23, 24 and 25, fasten the circuit board 21 to the housing 1. The wide leg 31 is fastened by standoff 24 while the upper portion 33 of the circuit board 21 is fastened by standoffs 23 and 25. The narrow leg 32 is not fastened, but rather is allowed to float. By using three standoffs 23, 24 and 25 while allowing the narrow leg 32 to float, the circuit board is adequately attached to the housing 1 while providing flexibility such that a twisting motion applied to the housing 1 will not cause fractures or other failures in the circuit board 21. This method of attachment allows the housing 1 to twist or stress while the circuit board 21 remains more rigid. Additionally, this allows the LED 9 (FIG. 1A) to remain better aligned to the photodiode 11 during such stress. Alternatively, the narrow leg 32 could be attached such that a hole holding a standoff has adequate free-play to allow the narrow leg freedom to remain unaffected by some twisting of the housing 1. The standoffs 23, 24 and 25, may be made, for example, from rubber, urethane, or other suitable materials. Still further, if a light diffuser is used over the LED 9, thus allowing for additional misalignment between the LED 9 and the photodiode 11, then the narrow leg 32 may be attached in a standard fashion as is the wide leg 31.

The foregoing described substrate transmittance meter 10 meets the requirements of being portable, accurate and reliable. However, this meter is unable to measure substrates or windows that do not have an accessible edge (a fixed window is defined as a window or substrate that has all edges surrounded, for example, a rear window that is non-movable, such that no edge is exposed for measurement purposes). The usefulness of the substrate transmittance meter 10 is improved and extended to further measure transmittances of fixed windows by the invention of the inventors herein. A problem of accurately measuring the transmittances of fixed windows is properly aligning a receiver and transmitter on opposing sides of the fixed window (the transmitter and receiver can no longer be mounted in a predetermined fixed relationship). The inventors herein provide a novel solution including providing a remote transmitter and a remote receiver, each having a donut shaped magnet that cause the remote transmitter and remote receiver to self align on opposing sides of the fixed window for making an accurate transmittance measurement.

Figure 7A:
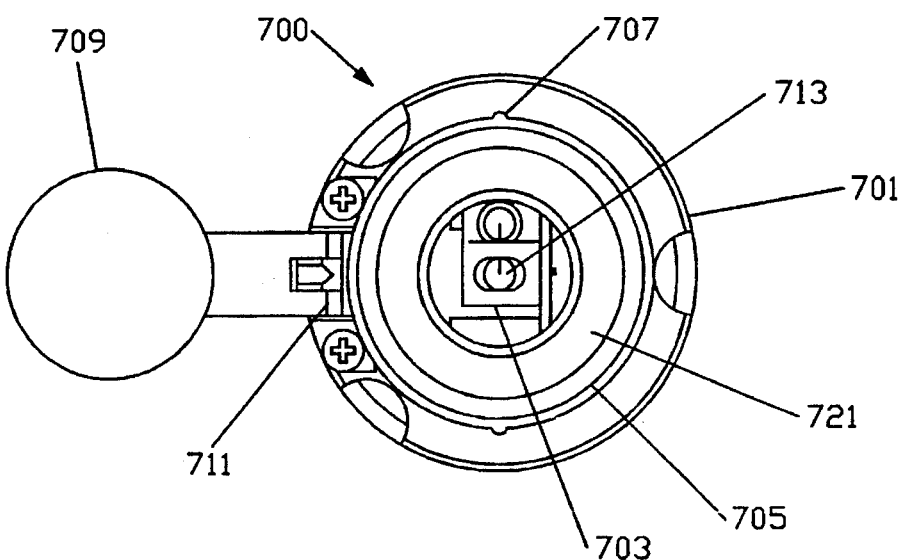
FIGS. 7A and 7B are bottom and side cutaway views, respectively, of a remote transmitter exposing a light transmitter therein according to a preferred embodiment of the present invention.
Figure 7B:
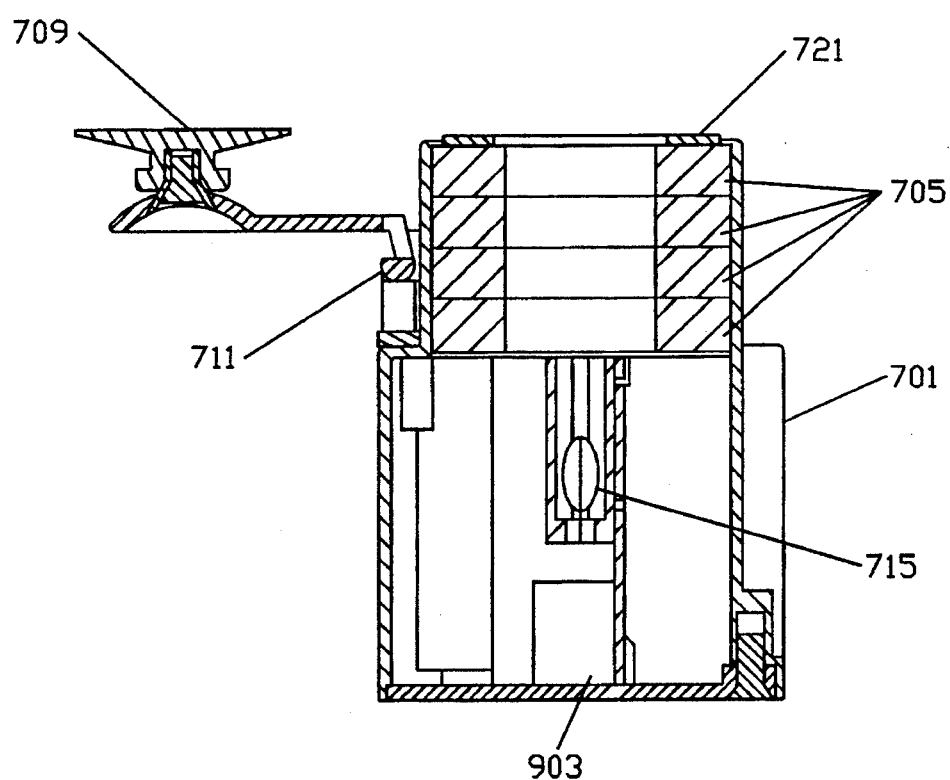

FIG. 7A depicts a remote transmitter 700 having a housing 701 with a suction cup 709 hingedly attached thereto by a hinge mechanism 711. The hinge mechanism 711 further includes a press fit snap that firmly holds the suction cup 709 against the housing 701 for storage purposes. Held within the housing 701 are a baffle 703 and light transmitter 713 which are similar in materials and purpose to the baffle 8 and light transmitter 9 as shown in FIG. 1A. The baffle 703 and light transmitter 713 are held in place and aimed through an opening in the housing 701 (coming out of the page). A light diffuser 715 (FIG. 7B) is provided covering the light transmitter 713 for diffusing the light thus allowing for some misalignment between the remote transmitter 700 and remote receiver 800 (approximately 10 millimeters).

One or more donut shaped magnets 705 (see FIG. 7B) are held in place at a bottom of the housing 701—the light transmitter is pointed through holes of the donut shaped magnets 705. The donut shaped magnets 705 are glued or otherwise permanently joined to form a cylinder type structure wherein magnetic flux lines of each magnet 705 are additive, i.e., the several magnets 705 join to form a single stronger magnet. A felt-like material 721 is attached to an outermost edge of the magnets 705 for interfacing with the substrate or window (providing both scratch protection and stray light blocking). Dual optical centering lines 707 are provided on the housing 701 for providing a visual indication of the internal location (optical center) of the light transmitter 713.

In operation, the light transmitter 713 (for example, an LED) receives a transmit signal for transmitting a light. If the substrate transmittance meter 10 is used as a base unit, the LED 9 is disabled and the light transmitter 713 receives the transmit signal (the signal that would have powered the LED 9, including LCLK). Alternatively, the light transmitter circuit 200, the light detector circuit 300 and display 500 may be integral to the remote transmitter 700 and/or remote receiver 800.

Figure 8A:
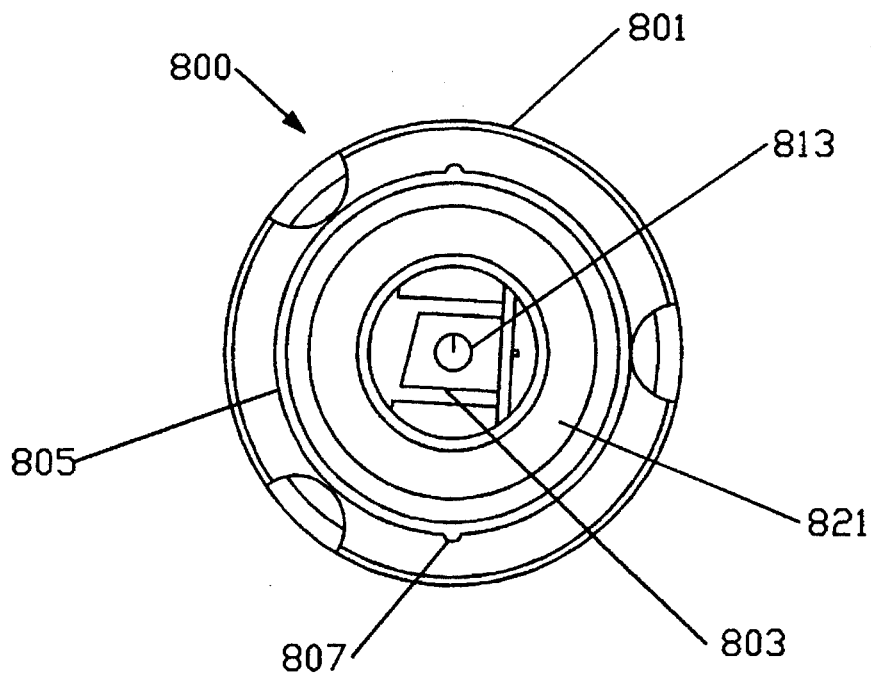
FIGS. 8A and 8B are top and side cutaway views, respectively, of a remote receiver exposing a light receiver therein according to a preferred embodiment of the present invention.

FIG. 8A depicts the remote receiver 800 having a housing 801. While there is not a suction cup attached to the housing 801, such a suction cup may be included on the housing 801 instead of or in addition to the housing 701 (FIG. 7) such that the remote receiver is releasably attached to the fixed window instead of the remote transmitter. Held within the housing 801 are a baffle 803 and light receiver 813 (i.e., a photodiode) which are similar in materials and purpose to the baffle 7 and light receiver 11 as shown in FIG. 1A. The baffle 803 and light receiver 813 are held in place for receiving a transmitted light through an opening in the housing 801 (going into the page).

Figure 8B:
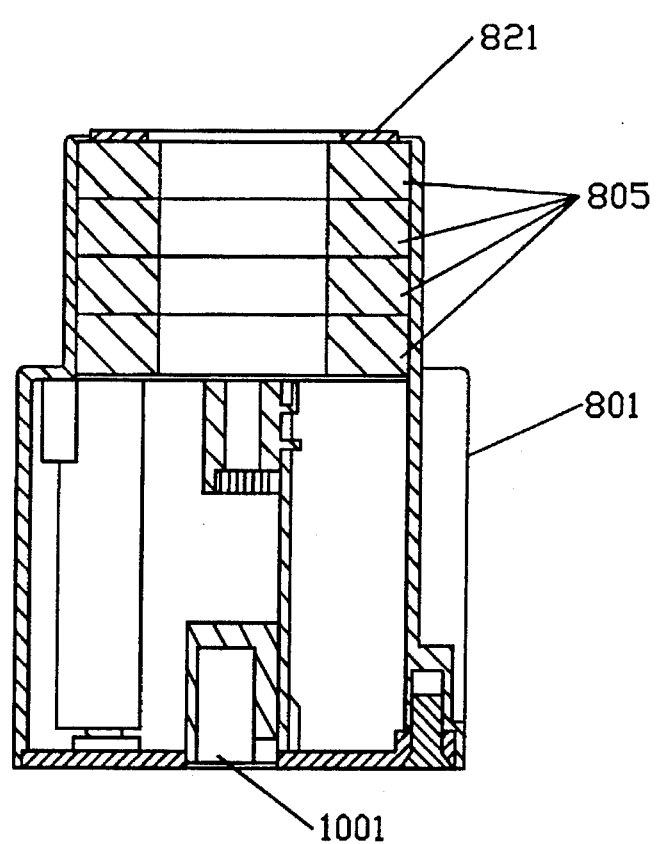

One or more donut shaped magnets 805 are held in place (FIG. 8B) at a bottom the housing 801—the light receiver 813 is pointed through a center of the holes of the donut shaped magnets 805. The donut shaped magnets 805 are glued or otherwise permanently joined to form a cylinder type structure wherein magnetic flux lines of each magnet 805 are additive, i.e., the several magnets 805 join to form a single stronger magnet (north poles connected to south poles). A felt-like material 821 (or other suitably soft material) is attached to an outermost edge of the donut shaped magnets 805 for interfacing with the substrate or window. Dual optical centering lines 807 are provided on the housing 801 for providing a visual indication of the internal location (optical center) of the light receiver 813 and for rotational alignment with the light transmitter 700.

In operation, the light receiver 813 receives the transmitted light from the remote transmitter 713 through the fixed window. If the substrate transmittance meter 10 is used as a base unit, the photodiode 11 is disabled and the light receiver 813 transmits a transmittance signal (VSIG, the signal that would have otherwise driven the display 500) to the base unit. Alternatively, the light transmitter circuit 200, the light detector circuit 300 and display 500 may be integral to the remote transmitter 700 and/or remote receiver 800.

METHOD OF OPERATION

Figure 9:
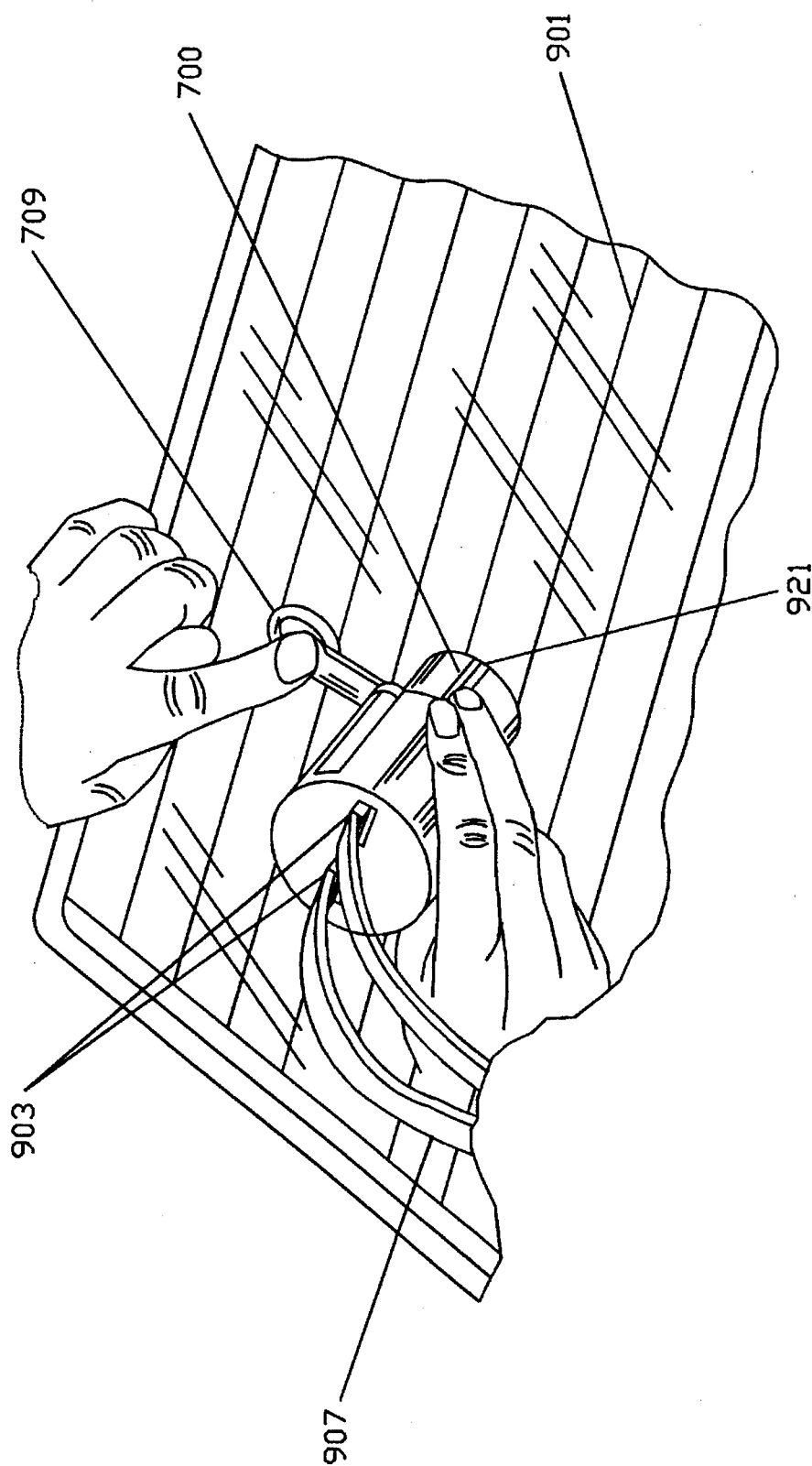
FIG. 9 is a pictorial drawing depicting attaching the remote transmitter to a fixed window according to a preferred embodiment of the present invention.

FIG. 9 shows the remote transmitter 700 being releasably attached to an outside surface of a fixed window. The suction cup 707 released from a storage position and swung away from the housing 701 about a hinge. The suction cup 709 is then attached to the outside surface of the fixed window such that optical centering lines are located between window defrost lines 901 if they are present. With the suction cup 709 attached to the fixed window the remote transmitter 700 rests against the outside surface of the fixed window wherein its own weight provides sufficient force to form a substantially light blocking interface between the felt-like material 921 and the fixed window.

Communication ports 903 accept wires for receiving the transmit signal from the base unit (if used) and for further receiving VSIG or its equivalent, the signal generated by the light receiver 813 as a result of measuring the transmitted light, and transmitting VSIG back to the base unit (if used).

Figure 10:
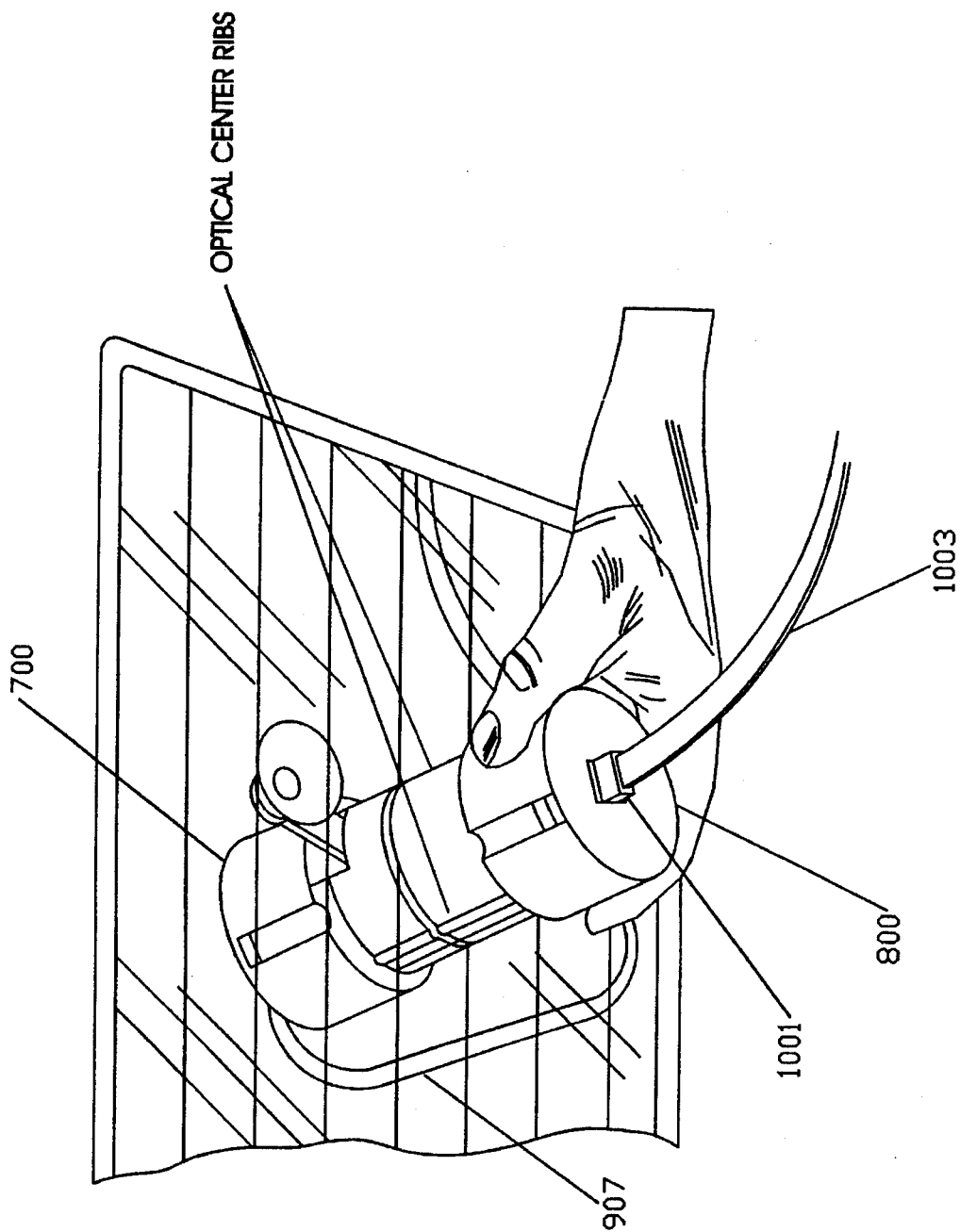
FIG. 10 is a pictorial drawing showing the self aligning step of coupling the remote receiver to the remote transmitter according to a preferred embodiment of the present invention.

FIG. 10 shows the relationship between the remote transmitter 700 and the remote receiver 800. The remote transmitter 700 is temporarily held in place and need not be moved again. The donut shaped magnets 805 of the remote receiver 800 is then brought near the inside or opposing surface of the fixed window near the donut shaped magnets 705 of the remote transmitter 700. The force of the magnetic flux lines of the donut shaped magnets 705 will attract the magnetic flux lines of the donut shaped magnets 805 and bring the remote receiver 800 into optical alignment with the remote transmitter (not rotational alignment but and edge-to-edge alignment). If there are defrost lines 901 in the fixed window the remote receiver 800 should be rotated so that the optical center ribs align on both units. If the fixed window does not have defrost lines 901, then the relationship of the optical center ribs is of no consequence.

Figure 11:
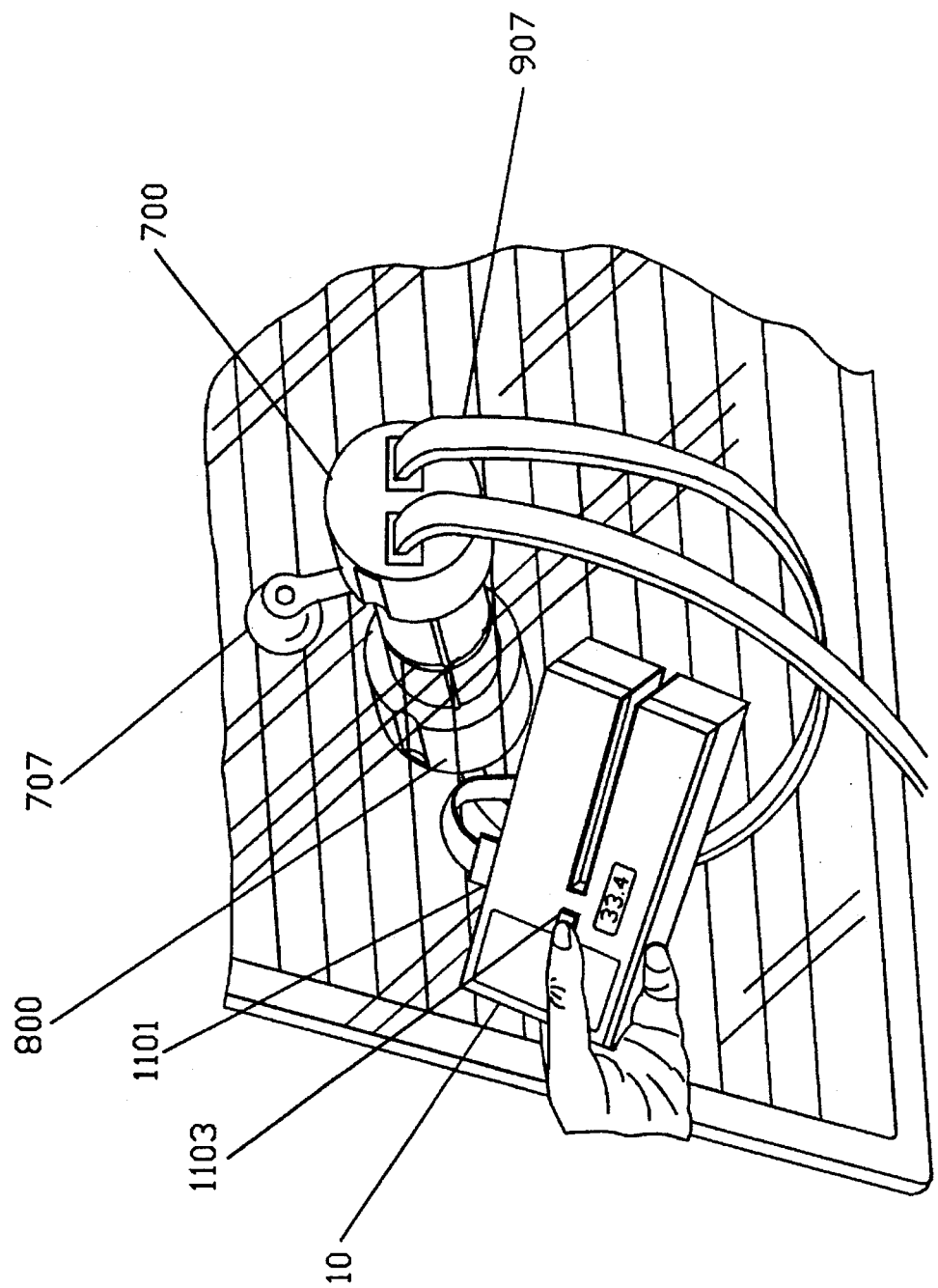
FIG. 11 is a pictorial drawing of the remote transmitter and remote receiver coupled to a base unit for measuring the window transmittance according to a preferred embodiment of the present invention.

FIG. 11 shows the transmittance measurement being performed with the remote transmitter 700 and the remote receiver 800 in place on the fixed window and coupled to the base unit 10. When the remote receiver 800 was brought into place near the remote transmitter 700, it was not necessary to attempt to exactly align the two remote units. The respective donut shaped magnets 705 and 805 self align the two units within a number of millimeters. A communication port 1101 on the base unit 10 causes the internal LED 9 and photodiode 11 to become disabled. The external light transmitter 713 and light receiver 813 receive the appropriate signals in place thereof. A transmittance measurement is enabled by pressing an enable switch 1103 on the base unit 10. The enable switch 1103 operates in place of the switch 5 of FIG. 1A. The resulting transmittance is then displayed on the base unit 10. While the remote transmitter 700 has been shown first attached on the outside surface of the fixed window, the remote receiver 800 could first be releasably attached to the outside surface of the fixed window with the remote transmitter 700 on the inside surface. The inside surface of the fixed window is the preferred location for locating the remote receiver 800 since the tinted fixed window would help block some stray light from reaching the remote receiver 800.

Although the present invention has been described in relation to particular embodiments thereof, many other variations and modifications and other uses will become apparent to those skilled in the art. For example, the materials chosen may vary so long as the physical and/or electrical requirements are met. The communication ports 903 and 1101 and the wires 907 can be replaced by other viable means of communication, for example, infrared or radio transmitted signals. The base unit 10 may not be necessary in the case where all of the electronics (less the LED 9 and photodiode 11) are integrated into the remote transmitter 700 and remote receiver 800 in some form. Furthermore, transmittance or opacity measurements are not meant to be limited to tinted glass or fixed automobile windows. Therefore, the present invention is limited only by the claims.

I claim:

1. A method for measuring a percent transmittance of a mounted substrate, wherein a transmitter houses a light transmitter and a first magnet, said light transmitter transmitting a light through an opening in said housing, and wherein a receiver houses a light receiver and a second magnet, said method comprising steps of:

placing said transmitter against a first surface of the mounted substrate with said first magnet substantially resting against the first surface such that said light transmitter is directed towards the first surface;

locating said remote receiver against an opposing surface of the mounted substrate with said second magnet substantially against said opposing surface and substantially in light path alignment with said transmitter;

allowing said receiver to self align to said transmitter according to first and second magnetic fields of said first and second magnets, respectively; and causing said light transmitter to emit a light through said mounted substrate for detection by said light receiver and measuring the percent transmittance of said mounted substrate.

2. The method according to claim 1 wherein said allowing step further comprises twisting said transmitter such that optical center ribs on said transmitter and said receiver are substantially aligned.

3. The method according to claim 1 wherein said allowing step further comprises twisting said receiver such that optical center ribs on said transmitter and said receiver are substantially aligned.

4. The method according to claim 1 wherein said mounted substrate is a fixed automobile window having first and second defroster lines therethrough, said allowing step further comprising substantially optically centering said transmitter between first and second defroster lines.

5. The method according to claim 1 further comprising:

coupling, electrically, said transmitter to said receiver; and further coupling, electrically, said transmitter and said receiver to a base unit.

6. A method of self aligning a remote transmitter on an outside surface of a fixed automobile window to a remote receiver on an inside surface of said fixed automobile window for measuring a transmittance of said fixed automobile window, said remote transmitter comprising a housing having a first magnet and a light transmitter and said remote receiver comprising a housing having a second magnet and a light receiver, wherein a base unit provides an input signal to and receives a transmittance signal from said remote transmitter and remote receiver, respectively, said method comprising the steps of:

coupling, electrically, said light transmitter to said light receiver and to said base unit;

temporarily placing said remote transmitter against said outside surface with said first magnet proximate said outside surface;

bringing said remote receiver proximate said inside surface and substantially directly across from said remote transmitter such that said second magnet is attracted towards said first magnet thereby causing said remote receiver to be in transmittance measuring alignment with said remote receiver; and measuring a transmittance of said fixed automobile window.

7. The method according to claim 6 wherein said remote transmitter further comprises a window attachment device for temporarily holding said remote transmitter in place against said outside surface.

8. The method according to claim 7 further comprising a step of aligning a center of said remote transmitter between first and second defroster lines in said fixed automobile window.

9. A self aligning window transmittance meter for measuring a light transmittance of a fixed window, comprising:

a remote transmitter having a first housing for holding a first magnet in a predetermined alignment with a light transmitter; and a remote receiver having a second housing for holding a second magnet in a predetermined alignment with a light receiver, said remote receiver capable to output a transmittance signal, wherein said remote transmitter is placed against a surface of said fixed window such that said remote receiver is brought proximate to an opposing surface of said fixed window and within a magnetic flux of said first magnet such that said first and second magnets are releasably held against said surface and opposing surface, respectively, so as to cause said remote transmitter and remote receiver to self align for measuring a light transmitted through said fixed window by said light transmitter and received by said light receiver for providing a light transmittance measurement of said fixed window.

10. The self aligning transmittance meter according to claim 9 further comprising a suction cup hingedly attached to said remote transmitter housing for releasably holding said remote transmitter in a resting position against said surface.

11. The self aligning transmittance meter according to claim 9 further comprising a suction cup hingedly attached to said remote receiver housing for releasably holding said remote receiver in a resting position against said opposing surface.

12. The self aligning transmittance meter according to claim 9 wherein said first and second magnets are donut shaped magnets and said light is transmitted through a center and received through a center of said first and second magnets, respectively.

13. The self aligning transmittance meter according to claim 9 wherein said first magnet and said second magnet each comprise a plurality of donut shaped magnets permanently held together.

14. The self aligning transmittance meter according to claim 9 further comprising a base unit for providing a transmit signal to said remote transmitter for causing said transmitted light to be output by said remote transmitter and receiving the transmittance signal from said remote receiver, said base unit having a display for displaying said transmittance measurement.

15. The self aligning transmittance meter according to claim 14 wherein each said first and second magnets comprise a soft material permanently attached to a surface thereof for interfacing between each said first and second magnet and said fixed window.

16. The self aligning window transmittance meter according to claim 9 wherein said remote transmitter and said remote receiver each comprise an optical centering rib thereon for identifying center locations of said light transmitter and said light receiver.

17. A portable light transmittance meter for measuring a light transmittance of vehicle windows, said light transmittance meter comprising:

- a base unit including a housing having a receptacle adapted for sliding over an edge of a vehicle window when said edge is accessible, said base unit further including a light transmitter circuit for transmitting a light through said vehicle window and a light detector circuit for receiving and measuring the light transmitted through said vehicle window, said measured transmitted light being displayed on a display of said base unit, said base unit having an override circuit comprising a communication port for providing a light transmit signal and receiving an external light transmitted signal and measuring said external light transmitted signal on said display;

- a remote transmitter having a first housing for holding a first donut shaped magnet in a predetermined alignment with a light transmitter, and having an input for receiving the transmit signal; and

- a remote receiver having a second housing for holding a second donut shaped magnet in a predetermined alignment with a light receiver, and having an output for transmitting the external transmit signal, wherein said remote transmitter is placed against a surface of said vehicle window such that said remote receiver is brought proximate to an opposing surface of said vehicle window and within a magnetic flux of said first donut shaped magnet such that said first and second donut shaped magnets are releasably held against said surface and opposing surface, respectively, so as to cause said remote transmitter and remote receiver to self align for measuring a light transmitted through said first and second donut shaped magnets and through said vehicle window by said light transmitter and received by said light receiver for providing the external transmitted light signal to said base unit.

18. The portable light transmittance meter according to claim 17 further comprising a suction cup hingedly attached to said remote transmitter for releasably holding said remote transmitter against said vehicle window.

19. The portable light transmittance meter according to claim 17 further comprising a suction cup hingedly attached to said remote receiver for releasably holding said remote receiver against said vehicle window.

\* \* \* \* \*